(12) United States Patent
Nikou

(10) Patent No.: US 11,076,919 B1
(45) Date of Patent: Aug. 3, 2021

(54) SURGICAL TOOL POSITION TRACKING AND SCORING SYSTEM

(71) Applicant: Smith & Nephew, Inc., Memphis, TN (US)

(72) Inventor: Constantinos Nikou, Monroeville, PA (US)

(73) Assignee: Smith & Nephew, Inc., Memphis, TN (US)

(*) Notice: Subject to any disclaimer, the term of this patent is extended or adjusted under 35 U.S.C. 154(b) by 478 days.

(21) Appl. No.: 15/985,369

(22) Filed: May 21, 2018

Related U.S. Application Data

(60) Provisional application No. 62/508,839, filed on May 19, 2017.

(51) Int. Cl.
*A61B 34/20* (2016.01)
*A61B 6/12* (2006.01)
*A61B 90/00* (2016.01)
*A61B 17/14* (2006.01)

(52) U.S. Cl.
CPC .............. *A61B 34/20* (2016.02); *A61B 6/12* (2013.01); *A61B 90/39* (2016.02); *A61B 17/147* (2016.11); *A61B 2034/2051* (2016.02); *A61B 2034/2055* (2016.02); *A61B 2090/0811* (2016.02)

(58) Field of Classification Search
CPC ............ A61B 34/20; A61B 6/12; A61B 90/00
See application file for complete search history.

(56) References Cited

U.S. PATENT DOCUMENTS

| | | | |
|---|---|---|---|
| 6,757,582 B2 | 6/2004 | Brisson et al. | |
| 7,815,644 B2* | 10/2010 | Masini | A61B 90/36 606/86 R |
| 8,961,536 B2 | 2/2015 | Nikou et al. | |
| 9,211,163 B1 | 12/2015 | Jaramaz et al. | |
| 9,855,106 B2 | 1/2018 | Jaramaz et al. | |
| 10,098,649 B2 | 10/2018 | Nikou et al. | |
| 10,105,152 B2 | 10/2018 | Nikou et al. | |
| 10,130,428 B2 | 11/2018 | Nikou et al. | |
| 10,194,966 B2 | 2/2019 | Corpa de la Fuente | |
| 10,251,706 B2 | 4/2019 | Jaramaz et al. | |
| 10,265,127 B2 | 4/2019 | Jaramaz et al. | |
| 10,368,878 B2* | 8/2019 | Lavallee | A61B 17/17 |
| 10,420,611 B2 | 9/2019 | Jaramaz et al. | |
| 10,452,238 B2 | 10/2019 | Nikou et al. | |
| 2009/0017430 A1* | 1/2009 | Muller-Daniels | G09B 23/30 434/262 |

* cited by examiner

*Primary Examiner* — Christopher J Beccia
(74) *Attorney, Agent, or Firm* — Troutman Pepper Hamilton Sanders LLP

(57) ABSTRACT

A system and method for tracking position and orientation of a surgical tool during a surgical procedure and providing feedback to a user are described. For example the system includes a surgical tool configured to perform at least a portion of the surgical procedure, a tracking system configured to monitor and record position information related to the surgical tool, a processing system, and a display. The processing system can be configured to receive the position information, determine optimal position information for the surgical tool during the surgical procedure, compare the received position information against the optimal position information to determine a conformance level for the user, and generate a user performance record. The display can be configured to receive and display the user performance record.

8 Claims, 7 Drawing Sheets

SURGICAL TOOL POSITION TRACKING AND SCORING SYSTEM

CROSS-REFERENCE TO RELATED APPLICATION

This application claims the benefit of priority to U.S. Provisional Application No. 62/508,839 titled "Surgical Tool Position Tracking and Scoring System," filed May 19, 2017, which is incorporated herein by reference in its entirety.

TECHNICAL FIELD

The present disclosure is generally related to apparatuses, systems and methods for computer-aided orthopedic surgery. More specifically, the present disclosure is related to automatically tracking and providing feedback to a user regarding the position and orientation of a surgical tool during a surgical procedure.

BACKGROUND

The use of computers, robotics, and imaging to aid orthopedic surgery is known in the art. There has been a great deal of study and development of computer-aided navigation and robotic systems used to guide surgical procedures. For example, a precision freehand sculptor employs a robotic surgery system to assist the surgeon in accurately cutting a bone into a desired shape. In procedures such as total hip replacement (THR) and total knee replacement (TKR), computer-aided surgery techniques have been used to improve the accuracy and reliability of the surgery. Orthopedic surgery guided by images has also been found useful in preplanning and guiding the correct anatomical position of displaced bone fragments in fractures, along a good fixation by osteosynthesis.

Cut guides or cutting blocks can be used in an orthopedic surgical procedure to assist a surgeon in cutting or modifying some portions of a target bone. For example, in joint replacement surgeries, such as THR or TKR, the preparation of the bones can involve temporarily affixing saw guide cutting blocks to the bones so that a reciprocating saw blade can be held steady along its intended path. Placement of these blocks can be guided by manual instrumentation or through the use of jigs.

The positioning of cutting blocks can be a time consuming and complicated process, which is critical to positive outcomes for the patient. Mechanisms that allow the cutting blocks to be adjusted within the required workspace are complex, and require high machining tolerances, adding to the cost and complexity of these instrument systems. In some cases, pins can be inserted into a patient's bone in order to provide an aligning mechanism for the cutting block. However, proper orientation and alignment of these pins becomes critical to properly placing the cutting block itself.

Computer-assisted surgical tools to aid with pin placement have started to become more prevalent. However, even these tools can lead to imprecise pin placement because the orientation and placement of the pin depends upon the user maintaining a drilling instrument at a proper angle and drilling to a proper depth through the drilling process. Imprecision when drilling pin placement holes can lead to improperly placed cutting blocks. If the cutting blocks are improperly placed, improper bone cuts, implant placement, and joint replacements can result.

SUMMARY

There is provided a system for tracking position and orientation of a surgical tool during a surgical procedure and providing feedback to a user. The system includes a surgical tool configured to perform at least a portion of the surgical procedure, the surgical tool including at least one tracking device, a tracking system configured to monitor the at least one tracking device and record position information related to the at least one tracking device during the surgical procedure, a processing system operably connected to the tracking system, and a display operably connected to the processing system. The processing system is configured to receive the position information from the tracking system, determine optimal position information for the surgical tool during the surgical procedure, compare the received position information against the optimal position information to determine a conformance level for the user, and generate a user performance record based on at least a portion of the conformance level. The display is configured to receive the user performance record and display the user performance record.

In some embodiments, the processing system is further configured to determine an actual cutting rate for the surgical tool during the surgical procedure, compare the actual cutting rate to an optimized cutting rate for the surgical tool to determine a user cutting performance, and update the user performance record to include the user cutting performance.

In some embodiments, the surgical tool is a rotating cutting device. In some additional embodiments, the processing system is further configured to determine a rotational speed for the rotating cutting device during the surgical procedure, compare the rotational speed to an optimized rotational speed for the rotating cutting device to determine a user operational performance, and update the user performance record to include the user operational performance.

In some embodiments, the user performance record includes information pertaining to the conformance level of one or more of a single surgical tool operation during the surgical procedure, a plurality of tool operations during the surgical procedure, and a plurality of tool operations performed by the user during the surgical procedure.

In some embodiments, the at least one tracking device includes a plurality of optical markers. In some additional embodiments, the plurality of optical markers are arranged in a known position on the surgical tool.

In some embodiments, the display is further configured to display the user performance record as a graphical display.

There is also provided a method for tracking position and orientation of a surgical tool during a surgical procedure and providing feedback to a user. The method includes monitoring, by a tracking system, at least one tracking device affixed to a surgical tool configured to perform at least a portion of the surgical procedure; recording, by the tracking system, position information related to the at least one tracking device; receiving, by a processing system operably connected to the tracking system, the position information from the tracking system; determining, by the processing system, optimal position information for the surgical tool during the surgical procedure; comparing, by the processing system, the received position information against the optimal position information to determine a conformance level for the user; generating, by the processing system, a user performance record based on at least a portion of the conformance level; receiving, by a display operable connected to the processing system, the user performance record; and displaying, by the display, the user performance record.

In some embodiments, the method further includes: determining, by the processing system, an actual cutting rate for the surgical tool during the surgical procedure; comparing, by the processing system, the actual cutting rate to an optimized cutting rate for the surgical tool to determine a user cutting performance; and updating, by the processing system, the user performance record to include the user cutting performance.

In some embodiments, the surgical tool is a rotating cutting device. In some additional embodiments, the method further includes determining, by the processing system, a rotational speed for the rotating cutting device during the surgical procedure; comparing, by the processing system, the rotational speed to an optimized rotational speed for the rotating cutting device to determine a user operational performance; and updating, by the processing system, the user performance record to include the user operational performance.

In some embodiments, the user performance record includes information pertaining to the conformance level of one or more of a single surgical tool operation during the surgical procedure, a plurality of tool operations during the surgical procedure, and a plurality of tool operations performed by the user during the surgical procedure.

In some embodiments, the at least one tracking device includes a plurality of optical markers. In some additional embodiments, the plurality of optical markers are arranged in a known position on the surgical tool.

In some embodiments, the method further includes displaying, by the display, the user performance record as a graphical display.

There is also provided a system for providing feedback to a user during a surgical procedure. The system includes a surgical tool configured to perform at least a portion of the surgical procedure and including at least one tracking device, a tracking system configured to monitor the at least one tracking device and record information related to the at least one tracking device during the surgical procedure, a processing system operably connected to the tracking system, and a display operably connected to the processing system. The processing system is configured to receive the information from the tracking system, determine current operational information for the surgical tool, compare the current operational information against optimal operation information for the surgical tool to determine a conformance level for the user, and generate a user performance record based on at least a portion of the conformance level. The display is configured to receive the user performance record and display the user performance record.

In some embodiments, the processing system is further configured to determine an actual cutting rate for the surgical tool during the surgical procedure, compare the actual cutting rate to an optimized cutting rate for the surgical tool to determine a user cutting performance, and update the user performance record to include the user cutting performance.

In some embodiments, the processing system is further configured to determine actual position information for the surgical tool from the information received from the tracking system, determine optimal position information for the surgical tool during the surgical procedure, compare the received position information against the optimal position information to determine a user position performance, and update the user performance record to include the user position performance.

The example embodiments as described above can provide various advantages over prior techniques. For example, the techniques as taught herein can more accurately provide real time feedback to a surgeon regarding their performance and efficiency during a surgical procedure. The techniques also provide for incentivizing a surgeon to improve their efficiency during a surgical procedure.

Further features and advantages of at least some of the embodiments of the present disclosure, as well as the structure and operation of various embodiments of the present disclosure, are described in detail below with reference to the accompanying drawings.

BRIEF DESCRIPTION OF THE DRAWINGS

Aspects, features, benefits and advantages of the embodiments described herein will be apparent with regard to the following description, appended claims, and accompanying drawings where:

DETAILED DESCRIPTION

Figure 1:
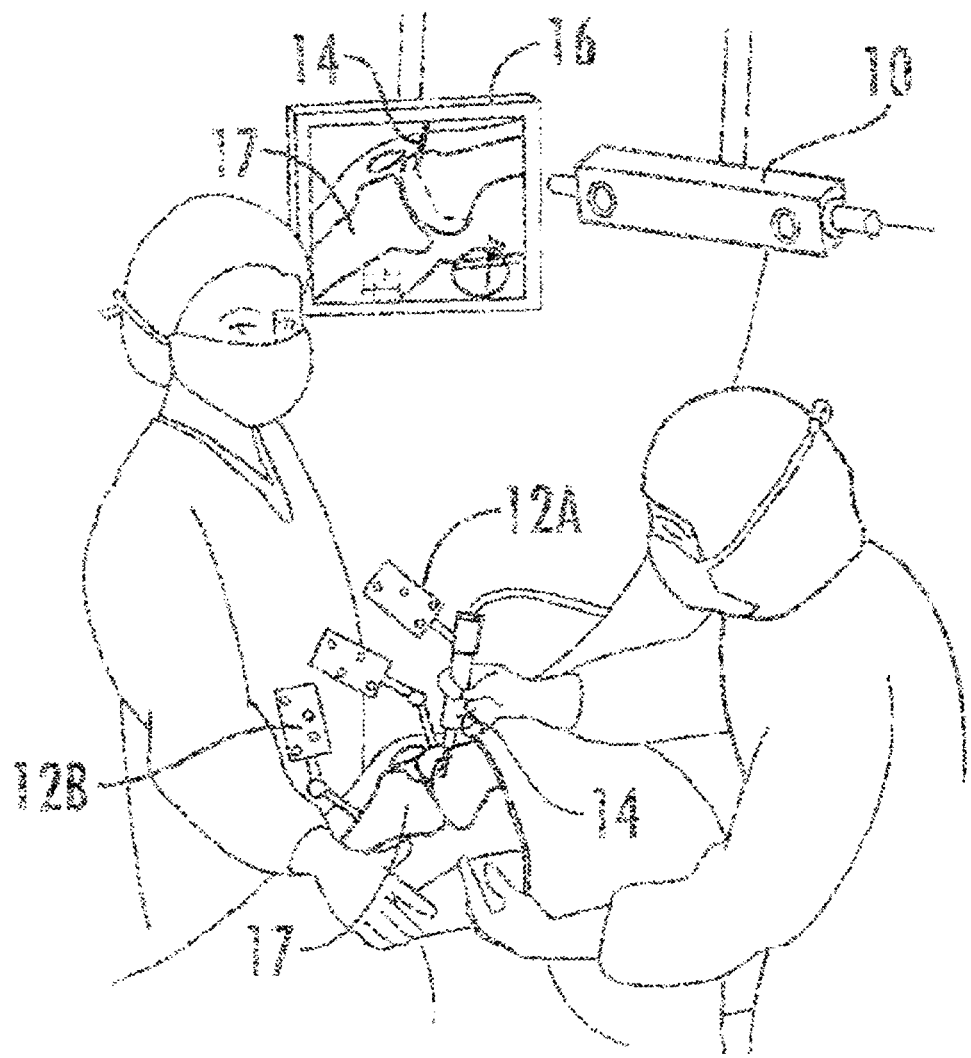
FIG. 1 depicts a simplified view of an illustrative optical surgical navigation setup during a joint replacement surgery in accordance with certain embodiments.

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

For purposes of the description hereinafter, the terms "upper", "lower", "right", "left", "vertical", "horizontal", "top" "bottom", "lateral" "longitudinal" and related derivatives thereof shall relate to the invention as it is oriented in the drawing figures. However, it is to be understood that the present invention may assume various alternative variations and step sequences, except where expressly specified to the contrary. It is also to be understood that the specific devices and processes illustrated in the attached drawings, and described in the following specification, are simply exemplary embodiments. For example, in the present disclosure, the surgical tool is described with respect to a surgical drill. However, any surgical tool on which a plurality of markers may be placed can be used within the scope of this disclosure. Moreover, specific dimensions and other physical characteristics related to the embodiments disclosed herein are not to be considered as unduly limiting.

Optical navigation is used in surgery to track a rigid body's location in space. FIG. 1 illustrates a simplified view of an illustrative surgical navigation setup having a tracking system such as, for example, an infrared camera 10 and a tracker 12A having a plurality of markers that may be used to perform surgical navigation. The tracker 12A may be rigidly attached to any object 14 that the user/surgeon wishes to track during the surgical procedure. The tracker 12A may include a defined configuration of markers (35 as shown in FIG. 3), such as infrared reflective markers, for example. The camera 10 may continuously take pictures of the workspace during the surgical procedure, and the markers 35 may be detected from those pictures. As will be understood by those of ordinary skill in the art, other position tracking systems may be used based on teachings of this disclosure including, but not limited to, electromagnetic, inertial, hybrid, etc.

Figure 2:
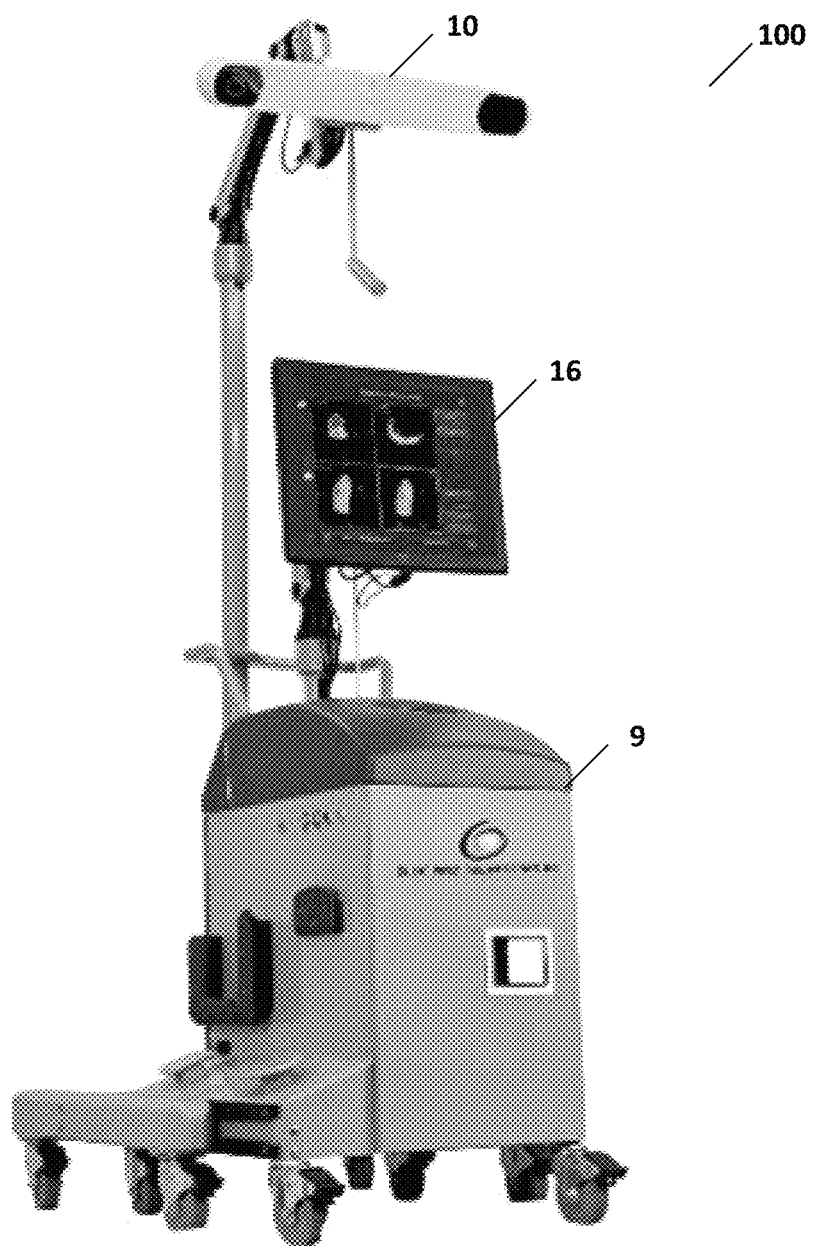
FIG. 2 depicts an illustrative navigation system in accordance with certain embodiments.

FIG. 2 depicts an illustrative navigation system 100 in accordance with certain embodiments. As shown in FIG. 2, the navigation system 100 may include an infrared camera 10, a processing system 9, and a display terminal 16. Using the known rigid spatial relationship of the markers 35 on the image frame obtained by the camera 10, the position (i.e., the location and orientation) of the object 14 in a 3D (three dimensional) space may be determined. The location of the object 14 may be continuously output to the processing system 9 that integrates this location with patient anatomy positional information that may be obtained, for example, from a CT scan or ultrasound image. As such, a determination of the location and orientation of the object 14 with respect to a remainder or reference position of the patient anatomy may be determined. The location and orientation of the object 14 relative to the patient anatomy, such as a bone 17, may also be continuously displayed on the display terminal 16. Thus, the user/surgeon may know and understand the location of the object 14 in relation to the bone 17.

In an embodiment, the display terminal 16 may be used to provide feedback information regarding various aspects of the surgical procedure, such as the orientation of the object 14. Further, the processing system 9 of the navigation system 100 may be used to determine the position and orientation of the object 14 with respect to a patient in substantially real time. Additional features and description of the detection and/or navigation system 100 may be found in, for example, U.S. Pat. Nos. 6,757,582 and 8,961,536, both of which are incorporated herein by reference in their entireties.

Figure 3A:
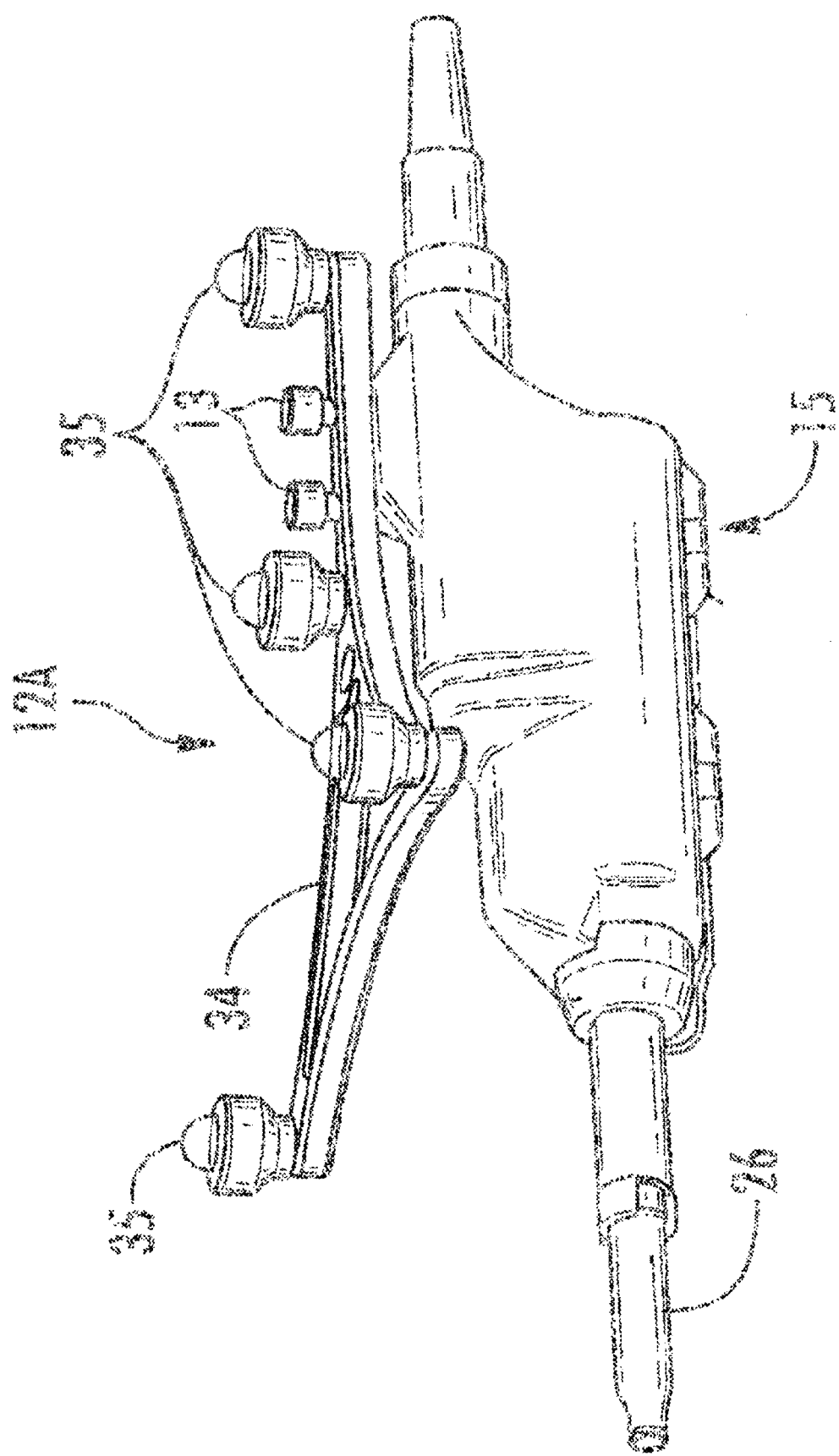
FIG. 3A depicts a perspective view of an embodiment of a handpiece having a plurality of markers attached thereto in accordance with certain embodiments.

FIG. 3A illustrates the tracker 12A, with tracker frame 34 and markers 35 rigidly attached to a rigid object to be tracked, such as a handpiece 15, for example. The tracking of the handpiece 15 allows the navigation system 100 to know the position of a distal end 22 of a drill 20 when the drill is inserted into the handpiece 15. In certain implementations, the tracker frame 34 may be relatively large as compared to the distal end 22 of the drill 20. Similar trackers, such as 12B, may be mounted, for example, on the bone 17 being operated on as shown in FIG. 1.

Display software may be used to project the geometry of the tracked object 14, such as, for example, the drill 20 having handpiece 15 thereon, on the display screen 16 so that a virtual, real-time image of the object 14 and the surrounding anatomy of the patient bone 17 can be made available to the user/surgeon to aid in the surgery. A virtual interface 16 may depict the tracked tool 20 within the handpiece 15 in geometrical relationship with the tracked anatomy 17 of a patient. This interface 16 may remain visible to the user/surgeon during a surgical procedure. It is understood that multiple objects may be tracked, including rigid patient anatomy, such as the bone 17, in the same workspace with the same camera 10. However, each tracked object or part of a patient's anatomy should have its own tracker frame/array and the configuration of the markers should be unique for each object so as to enable the software, or any other computer processor analyzing image data, to distinguish between objects based on their respective trackers.

Figure 3B:
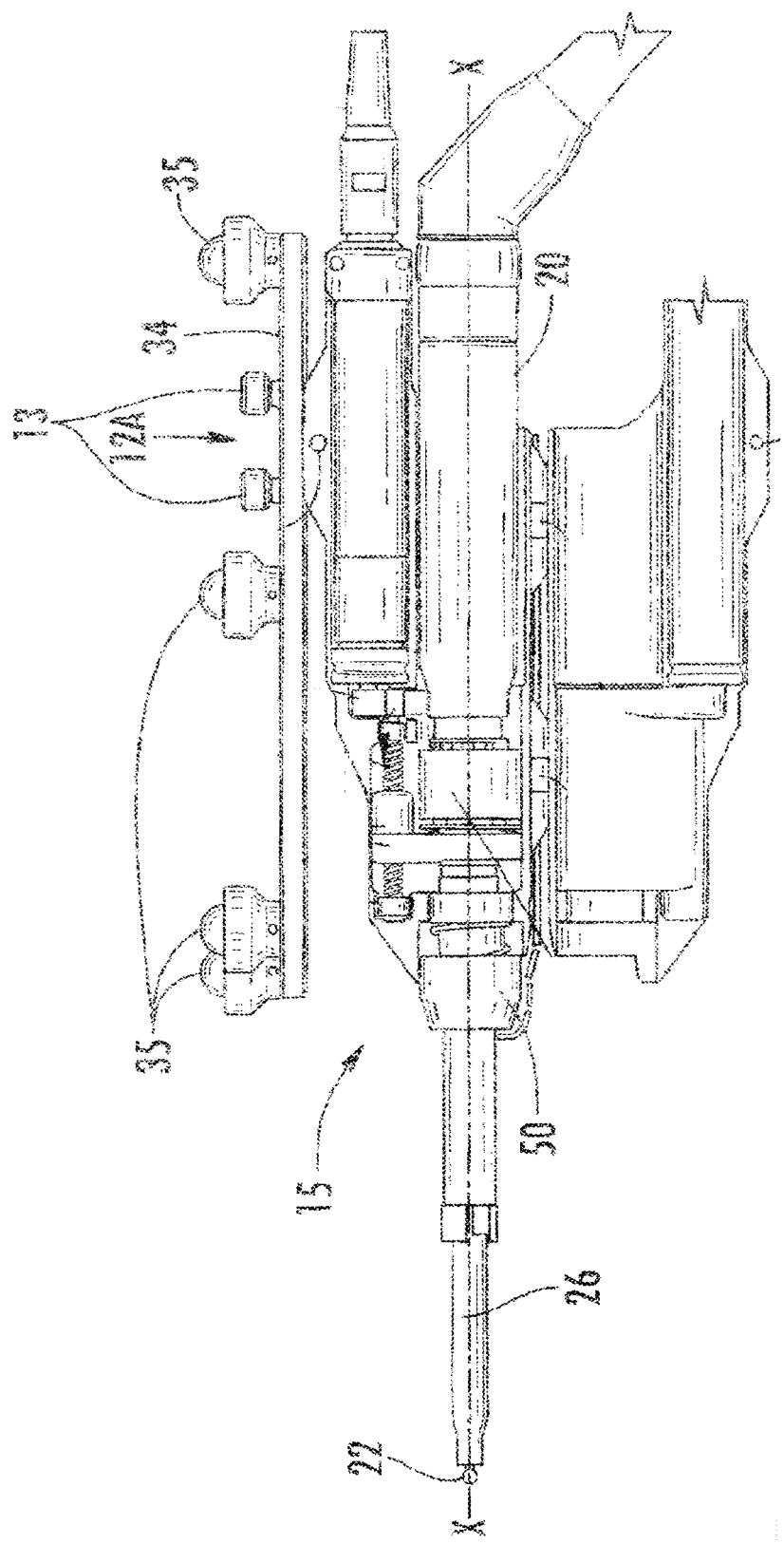
FIG. 3B depicts a plan view of a handpiece in an opened position having a surgical tool positioned therein in an extended position in accordance with certain embodiments.

FIG. 3B depicts a side view of an opened handpiece 15 with the tracker 12A attached thereto with mounting members 13 and the drill 20 inserted in a partially extended position therein. When the drill 20 is inserted into the handpiece 15, the distal end 22 and a proximal end of the drill 20 may each be in a fixed position with respect to the markers 35 of the tracker 12A because of the rigid attachment of the marker frame 34 to the handpiece. As such, a location of the distal end 22 and the proximal end of the drill 20 may be determined by the processing system 9.

The handpiece 15 may include a modular guard 26 to control exposure of the distal end 22 of a drill 20 inserted into the handpiece. The outer housing of the handpiece may include a locking mechanism 50 for easy attachment and detachment of the modular guard 26.

Although the markers described above depict a tracker frame 34 having markers 35 attached thereto in a known configuration, alternate configurations of markers may be used. For example, at least one distal marker may be placed on or near a distal end of a drill and at least one proximal marker may be placed on or near a proximal end of the drill. The at least one distal marker and the at least one proximal marker may be placed directly on the drill in a known configuration. In an alternate embodiment, the at least one distal marker and the at least one proximal marker may be placed on a handpiece in a known configuration. Other marker configurations may also be used within the scope of this disclosure.

In some embodiments, information pertaining to the orientation and position of a surgical tool may be useful to a surgeon performing a surgical procedure. For example, when the surgeon is performing a drilling operation using a drill 20, the surgeon or others may be interested in determining whether the hole being drilled is in the proper position, at the proper orientation, drilled to the proper depth, or the like.

Figure 4:
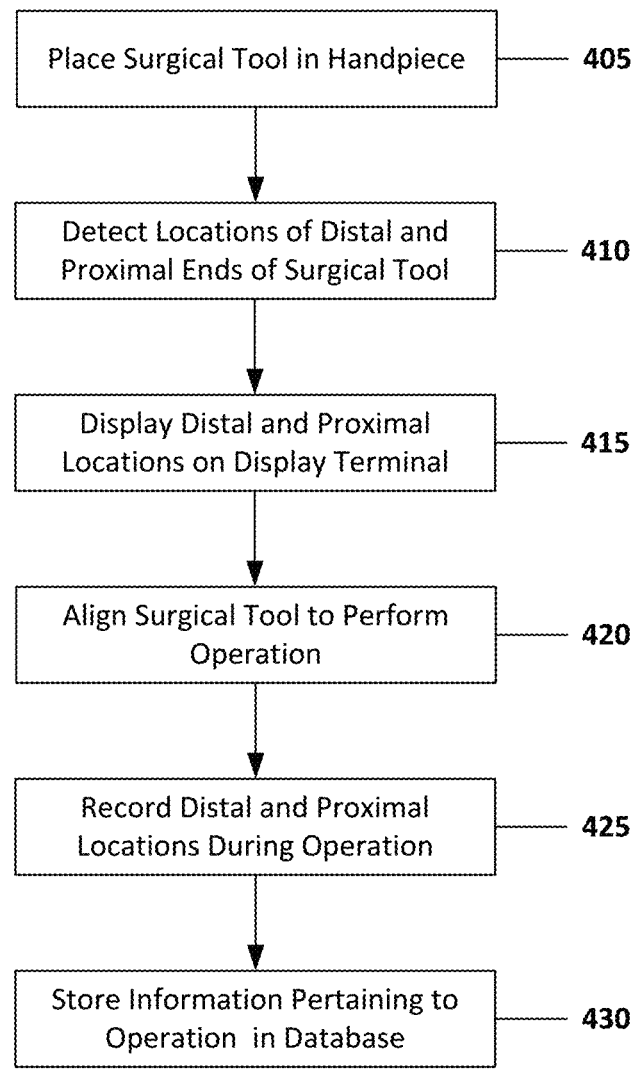
FIG. 4 depicts a flow diagram of an illustrative method of automatically tracking and providing feedback to a user regarding the position and orientation of a surgical tool during a surgical procedure in accordance with certain embodiments.

FIG. 4 depicts a flow diagram of an illustrative method of automatically tracking and providing feedback to a user regarding the position and orientation of a surgical tool during a surgical procedure in accordance with certain embodiments. As shown in FIG. 4, a surgical tool, such as a drill, may be placed 405 in a handpiece prior to performing a surgical operation, such as a drilling operation. The handpiece may be similar to the ones described above in reference to FIGS. 3A and 3B or any other handpiece that is able to be tracked via a navigation system, such as the one described above in reference to FIG. 2.

The locations of the distal and proximal ends of the surgical tool may be detected 410 using the tracking system. For example, the tracking system may detect 410 the location of the markers on a tracking frame attached to the handpiece. Based on pre-programmed information pertaining to the relative sizes and positions of the handpiece, the drill and the markers on the tracking frame, a location of a distal end of the drill and a proximal end of the drill in three dimensional space may be determined. Methods of determining a location of a distal end and a proximal end of a surgical tool will be apparent to those of ordinary skill in the art based on this disclosure.

The locations of the distal and proximal ends of the surgical tool may be displayed 415 on a display terminal. For example, the display terminal may display 415 graphical or alphanumerical information pertaining to the locations of the distal and proximal ends of the surgical tool with respect to a point in three dimensional space at which a drilling operation is to commence. Further information regarding displaying 415 the locations of the distal and proximal ends of the surgical tool are disclosed below in reference to FIGS. 5A-D.

The surgical tool may be aligned 420 to perform a surgical operation. For example, the user may review the information displayed 415 on the display terminal and use the information as a guide to align 420 the surgical tool before commencing the surgical operation. For example, the user may manipulate the position and orientation of the surgical tool to align displayed indicators representing the distal and proximal ends of the surgical tool, thereby indicating that the tool is aligned at a proper angle for performing the surgical operation.

As the surgical operation is being performed, location information pertaining to the distal end and the proximal end of the surgical tool may be recorded 425. In an embodiment, the location information may be graphically displayed on the display terminal as part of the recording process 425.

Information pertaining to the surgical operation may be stored 430 in a database or other similar data structure. For example, the information may include the locations of the distal end and the proximal end of the surgical tool throughout the surgical operation, assessment information regarding the accuracy of the user when performing the surgical operation, historical accuracy information regarding the user and/or one or more other users, or the like. Further examples of the types of information that may be stored are discussed below in reference to FIGS. 5A-D.

Figure 5A:
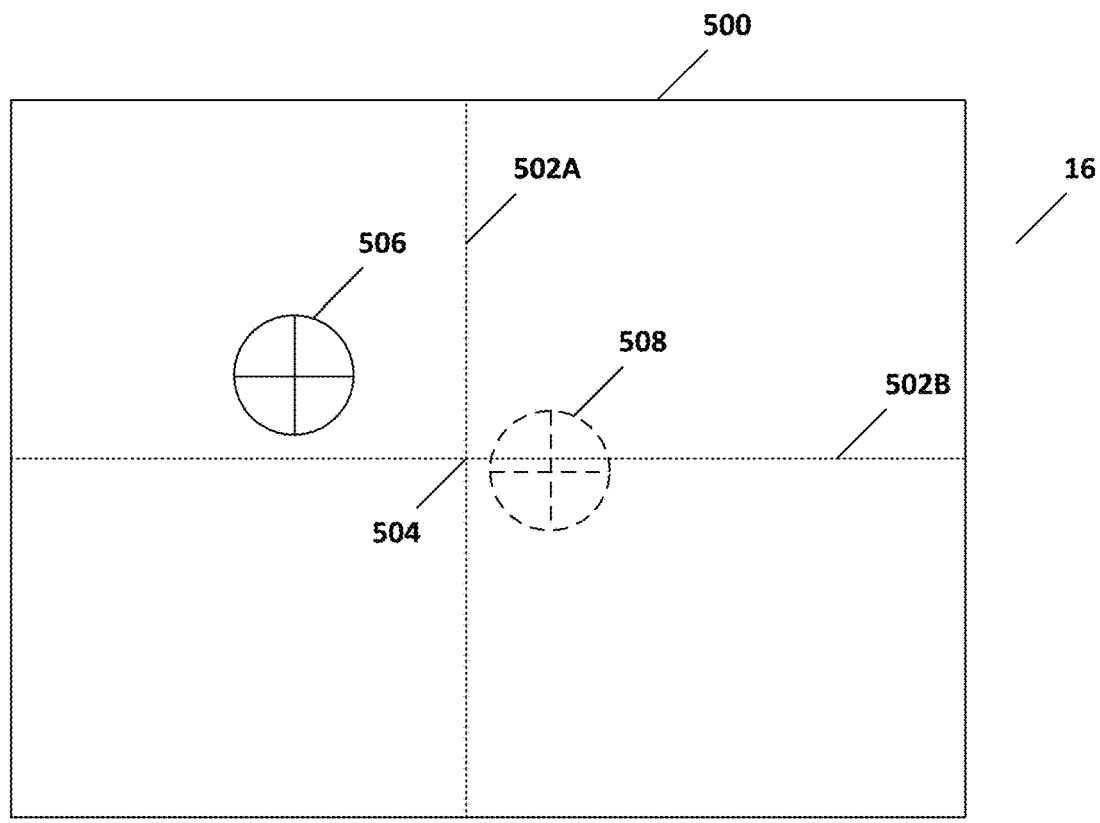
FIGS. 5A-D depict illustrative displays for providing position tracking information in accordance with certain embodiments.

FIGS. 5A-D depict illustrative displays for providing position tracking information in accordance with certain embodiments. As shown in FIG. 5A, the display screen 16 may display a representation 500 of the tracked objects within the surgical space. Within the displayed representation 500, the display screen 16 may include directional axes 502A,B identifying a position at which a drill hole should be placed at their intersection 504. In addition, the displayed representation 500 may include a first crosshair 506 representative of the location of the distal end of the drill and a second crosshair 508 representative of the location of the proximal end of the drill. If the position of the drill (as represented by the distal end and the proximal end) is perfectly aligned to drill a particular hole, both of the crosshairs 506, 508 may be coincident with the intersection point 504 of the directional axes 502A,B. Alternate signifiers may be used in place of the crosshairs 506, 508 as will be apparent to one of ordinary skill in the art based on this disclosure.

Figure 5B:
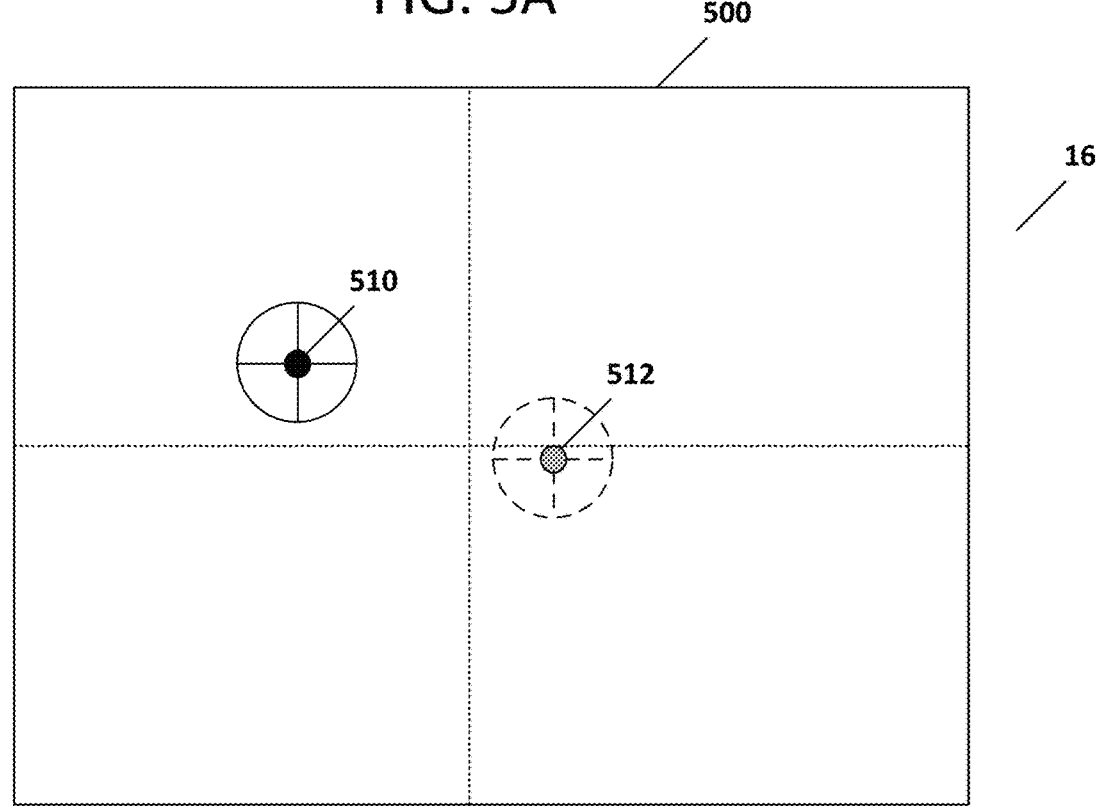

When a drilling operation commences, the displayed representation 500 may identify the position of the distal end of the drill and the proximal end of the drill at various points in time. For example, as shown in FIG. 5B, the displayed representation may include a first mark 510 representing the location of the distal end of the drill at the time that the drilling operation commenced and a second mark 512 representing the location of the proximal end of the drill at the time that the drilling operation commenced. Although the marks 510, 512 are shown in different shading in FIG. 5B, it will be apparent to one of ordinary skill in the art that the marks may differ in color, shade, shape, style or any other distinguishing feature to allow a user to identify whether a mark was placed based on the location of the distal end or the location of the proximal end during the drilling operation.

Figure 5C:
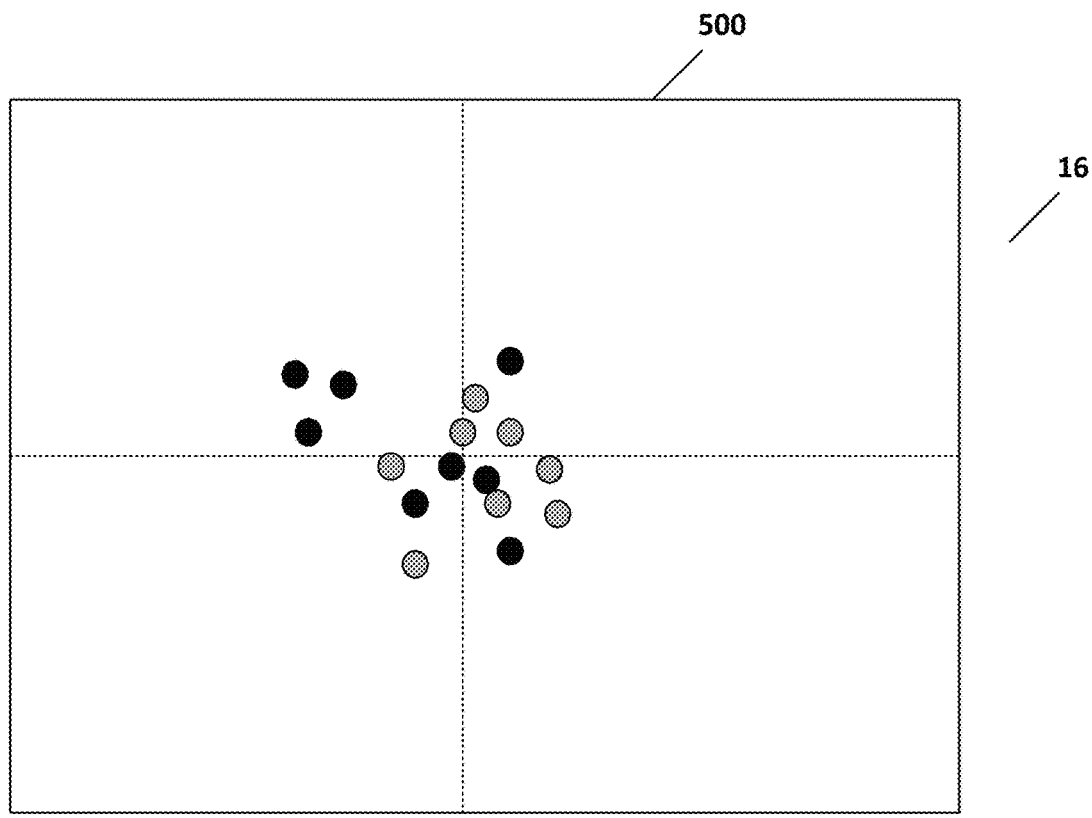

As shown in FIG. 5C, during the drilling operation a plurality of locations may be recorded for each of the distal end of the drill and the proximal end of the drill in the displayed representation 500. In an embodiment, a mark may be recorded for each of the distal end of the drill and the proximal end of the drill at a determined time interval. For example, a mark may be recorded for each of the distal end of the drill and the proximal end of the drill at a determined time interval of about 1 microsecond (µs), about 10 µs, about 20 µs, about 50 µs, about 100 µs, about 200 µs, about 500 µs, about 1 millisecond (ms), about 2 ms, about 5 ms, about 10 ms, about 20 ms, about 50 ms, about 100 ms, about 200 ms, about 500 ms, or about 1 second, or within a time interval bounded by any two of the aforementioned time periods.

In an embodiment, the location of the distal end of the drill and the proximal end of the drill during the drilling operation may be represented as discrete points as in FIG. 5C. In an alternate embodiment, the location of the distal end of the drill and the proximal end of the drill during the drilling operation may be represented as a continuous path. Other methods of displaying the locations of the distal and proximal ends of the drill will be apparent to one of ordinary skill in the art based on this disclosure.

Figure 5D:
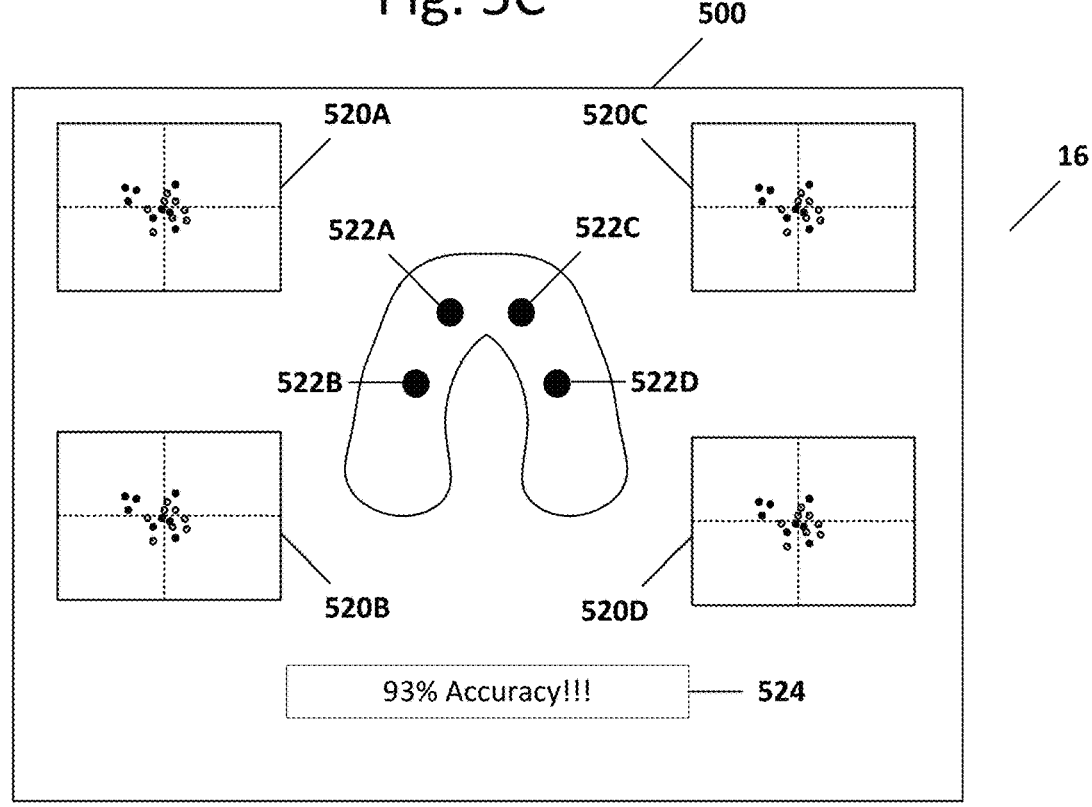

FIG. 5D depicts a final assessment screen for a surgical procedure. As shown in FIG. 5D, graphs 520A-D of the distal end of the drill and the proximal end of the drill for each of a plurality of drilling operations may be displayed in the displayed representation 500. In an embodiment, a diagram of the particular drilling positions 522A-D and a drilling guide may be displayed in the displayed representation 500 as well. In an embodiment, feedback information 524 may be provided to the user as an assessment of the accuracy of their drilling as compared to an ideal drilling operation.

The feedback information 524 may be presented to the user during the surgical operation. In addition, the feedback information 524 may be recorded in a database entry associated with the user to assess the user's performance. For example, the feedback information 524 may be used by the user, a supervisor, a vendor, a manufacturer, or any other individual or entity to assess performance of the user as compared to other users and/or as compared to the user's past performance. In this manner, the user may be incentivized to increase their proficiency based on such comparison. In addition, incentives may be provided to users that are the most accurate across a plurality of surgical procedures, or to users that show the most improvement in their accuracy in a given period of time.

In certain implementations, to improve efficiency during a surgical procedure, the surgeon may be incentivized to maintain particular levels of performance during a surgical procedure. For example, when burring, the feedback information 524 may also include a scale or meter that provides a visual indication of real-time performance. The meter may reflect, for example, a readout indicative of the amount of material the surgeon is removing for a given time period. For example, when planning a surgical procedure, the amount of bone to be removed may be measured in voxels included on a 3D representation of the bone. The feedback information 524 may include, for example, a VPM meter showing a measurement of voxels per minute that the surgeon is removing, similar to a miles per gallon fuel measurement included in vehicles that are intended to promote more efficient driving. For a specific cut, there may be an optimized cutting rate that combines high accuracy with high efficiency. By providing feedback showing how close a surgeon is to hitting that optimized cutting rate, the surgeon may be more incentivized to maintain their cutting speed as close to the optimized cutting rate as possible.

Similarly, the feedback information 524 can include a measurement of the rotational speed of the cutting bur. For example, for a particular bur, there may be an optimal rotational speed for optimal cutting. The feedback information 524 can provide an indication as to whether the bur is rotating too slowly (resulting in inefficient cuts) or too fast (potentially resulting in inaccurate cuts).

Results directed to both the optimized cutting rate of bone as well as operating the cutting tool at an optimal speed can be collected as described above and included when determining a final score for a surgeon during a procedure. As such, both the optimized cutting rate of bone as well as operating the cutting tool at an optimal speed can be important factors for incentivizing a surgeon to improve their performance during a surgical procedure, thereby improving their efficiency and potential earnings.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A method for tracking position and orientation of a surgical tool having distal and proximal ends during a surgical procedure and providing feedback to a user, the method comprising:
    receiving, by a processing system operably connected to a tracking system, position information for at least one tracking device affixed to the surgical tool from the tracking system;
    determining, by the processing system, a location for the distal end and the proximal end of the surgical tool in three-dimensional space based on the received position information for the at least one tracking device to identify the position and orientation of the surgical tool;
    comparing, by the processing system, the identified position and orientation of the surgical tool to optimal position and orientation data to determine a conformance level for the user for the surgical procedure; and
    generating, by the processing system, a user performance record based on at least a portion of the conformance level.

2. The method of claim 1, further comprising:
    determining, by the processing system, an actual cutting rate for the surgical tool during the surgical procedure;
    comparing, by the processing system, the actual cutting rate to an optimized cutting rate for the surgical tool to determine a user cutting performance; and
    updating, by the processing system, the user performance record to include the user cutting performance.

3. The method of claim 1, wherein the surgical tool is a rotating cutting device.

4. The method of claim 3, further comprising:
    determining, by the processing system, a rotational speed for the rotating cutting device during the surgical procedure;
    comparing, by the processing system, the rotational speed to an optimized rotational speed for the rotating cutting device to determine a user operational performance; and
    updating, by the processing system, the user performance record to include the user operational performance.

5. The method of claim 1, wherein the user performance record comprises information pertaining to the conformance level of one or more of a single surgical tool operation during the surgical procedure, a plurality of tool operations during the surgical procedure, and a plurality of tool operations performed by the user during the surgical procedure.

6. The method of claim 1, wherein the at least one tracking device comprises a plurality of optical markers.

7. The method of claim 6, wherein the plurality of optical markers are arranged in a known position on the surgical tool.

8. The method of claim 1, further comprising displaying, by the display, the user performance record as a graphical display.

* * * * *